United States Patent
DeLuca et al.

(10) Patent No.: US 6,894,037 B2
(45) Date of Patent: May 17, 2005

(54) 2-METHYLENE-19-NOR-20(S)-25-METHYL-1α-HYDROXYCALCIFEROL AND ITS USES

(75) Inventors: Hector F. DeLuca, Deerfield, WI (US); Pawel K. Grzywacz, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/657,533

(22) Filed: Sep. 8, 2003

(65) Prior Publication Data

US 2005/0004085 A1 Jan. 6, 2005

Related U.S. Application Data

(63) Continuation-in-part of application No. 10/613,201, filed on Jul. 3, 2003.

(51) Int. Cl.$^7$ .................... A61K 31/593; C07C 401/00
(52) U.S. Cl. ....................................... 514/167; 552/653
(58) Field of Search ........................ 514/167; 552/653

(56) References Cited

U.S. PATENT DOCUMENTS

| | | | |
|---|---|---|---|
| 4,666,634 A | 5/1987 | Miyamoto et al. | |
| 4,800,198 A | 1/1989 | DeLuca et al. | |
| 5,086,191 A | 2/1992 | DeLuca et al. | |
| 5,089,641 A | 2/1992 | DeLuca et al. | |
| 5,237,110 A | 8/1993 | DeLuca et al. | |
| 5,246,925 A | 9/1993 | DeLuca et al. | |
| 5,536,713 A | 7/1996 | DeLuca et al. | |
| 5,578,587 A | 11/1996 | DeLuca et al. | |
| 5,587,497 A | 12/1996 | DeLuca et al. | |
| 5,817,648 A | 10/1998 | Kutner et al. | |
| 5,843,927 A | 12/1998 | DeLuca | |
| 5,843,928 A * | 12/1998 | Deluca et al. | 514/167 |
| 5,846,960 A | 12/1998 | Labrie | |
| 5,849,726 A | 12/1998 | Brenner | |
| 5,877,168 A | 3/1999 | Miyamoto et al. | |
| 5,936,133 A | 8/1999 | DeLuca et al. | |
| 5,945,410 A | 8/1999 | DeLuca et al. | |
| 6,114,317 A * | 9/2000 | DeLuca et al. | 514/167 |
| 6,392,071 B1 * | 5/2002 | DeLuca et al. | 552/653 |
| 6,696,431 B2 * | 2/2004 | DeLuca et al. | 514/167 |

FOREIGN PATENT DOCUMENTS

| | | |
|---|---|---|
| EP | 0184206 | 12/1985 |
| EP | 0078704 | 4/1987 |
| EP | 0387077 | 9/1990 |
| EP | 0480572 | 4/1992 |
| EP | 0474517 | 11/1992 |
| EP | 0516410 | 12/1992 |
| WO | WO90/09991 | 9/1990 |
| WO | WO96/01811 | 1/1996 |

OTHER PUBLICATIONS

Chemical Abstracts, XP–00206605, vol. 121, No. 21, Nov. 21, 1994.

Posner et al, "2–Fluoroalkyl A–Ring Analogs of 1,25–Dihydroxyvitamin D3–Stereocontrolled Total Synthesis via Intramolecular and Intermolecular Diels–Alder Cycloadditions. Preliminary Biological Testing", Journal of Organic Chemistry, 60, pp. 4617–4628, 1995.

Slatopolsky et al, "A New Analog of Calcitriol, 19–Nor–1, 25–(OH)2 D2 Supresses Parathyroid Hormone Secretion in Uremaic Rats in the Absence of Hypercalcemia", American Journal of Kidney Disorders, 26(5), 832–60, 1995.

Posner et al, "Stereocontrolled Synthesis of a Trihydroxylated A Ring as an Immediate Precursor to 1Alpha,2Alpha, 25–Trihydroxyvitamin D3", Journal of Organic Chemistry, 56, pp. 4339–4341, Apr. 15, 1995.

(Continued)

Primary Examiner—Barbara P. Badio
(74) Attorney, Agent, or Firm—Andrus, Sceales, Starke and Sawall, LLP

(57) ABSTRACT

This invention provides a novel vitamin D analog, namely, 2-methylene-19-nor-20(S)-25-methyl-1α-hydroxycalciferol. The compound has the formula:

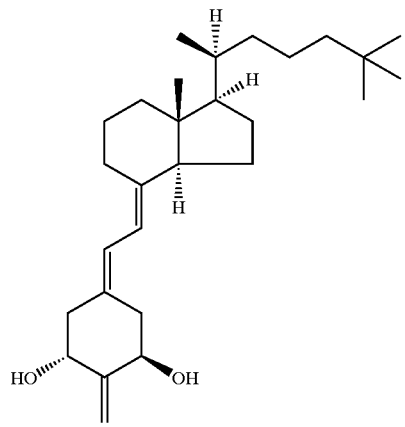

This 2-substituted compound is characterized by relatively high intestinal calcium transport activity and relatively low bone calcium mobilization activity resulting in novel therapeutic agents for the treatment of diseases where bone formation is desired, particularly osteoporosis. These compounds also exhibit pronounced activity in arresting the proliferation of undifferentiated cells and inducing their differentiation to the monocyte thus evidencing use as anti-cancer agents and for the treatment of diseases such as psoriasis.

31 Claims, 3 Drawing Sheets

OTHER PUBLICATIONS

Chemical Abstracts, "Chemistry of Synthetic High Polymers", vol. 110, No. 10, Abstract 110: 82505v, Mar. 6, 1989.

Okano et al, "Regulatory Activities of 2Beta–(3–Hydroxypropoxy)–1Alpha,25–Dihydroxyvitamin D3. A Novel Synthetic Vitamin D3 Derivative on Calcium Metabolism", Biochemical and Biophysical Research Communications, vol. 163, No. 3, pp. 1444–1449, Sep. 29, 1989.

Bouillon et al, "Biological Activity of Dihydroxylated 19–Nor–(Pre)Vitamin D3", Bioactivity of 19–Nor–Pre D, vol. 8, No. 8, pp. 1009–1015, 1993.

Sarandeses et al, "Synthesis of 1Alpha, 25–Dihydroxy–19–Norprevitamin D3", tetrahedron Letters, pp. 5445–5448, Apr. 1992.

Perlman et al, "1Alpha,25–Dihydroxy–19–Nor–Vitamin D3, A Novel Vitamin D–Related Compound with Potential Therapeutic Activity", Tetrahedron Letters, vol. 31, No. 13, pp. 1823–1824, Feb. 1990.

Baggiolini et al, "Stereochemical Total Synthesis of 1Alpha, 25–Dihydroxycholecalciferol and 1Beta,25–Dihydroxyerocalciferol", Journal of Organic Chemistry, 51, pp. 3098–3108, 1986.

Kiegiel et al, "Chemical Conversion of Vitamin D3 to its 1,25–Dihydroxy Metabolite", Tetrahedron Letters, vol. 31, No. 43, pp. 6057–60660, 1991.

Sicinski et al, "New 1Alpha,25–Ihydroxy–19–Norvitamin D3 Compounds of High Biological Activity: Synthesis and Biological Evaluation of 2–Hydroxymethyl, 2–Methyl, and 2–Methylene Analogues", Journal of Medical Chemistry, 41, pp. 4662–4674, 1998.

Brown et al, "New Active Analogues of Vitamin D with Low Calcemic Activity", Kidney International, vol. 38, Suppl. 29, 1990, pp. S–22–S–27.

Hareau et al, "Asymmetric Synthesis of 1Alpha,25–Dihydroxyvitamin D3 A–Ring Precursor Starting with 5–Tert–Butyldimethylsiloxy–2–Cyclohexenone", Tetrahedron Letters, 41, 2000, pp. 2385–2388.

* cited by examiner

2-METHYLENE-19-NOR-20(S)-25-METHYL-1α-HYDROXYCALCIFEROL AND ITS USES

CROSS-REFERENCE TO RELATED APPLICATION

This application is a continuation-in-part of application Ser. No. 10/613,201 filed on Jul. 3, 2003.

BACKGROUND OF THE INVENTION

This invention relates to vitamin D derivatives substituted at the carbon 2 position, and more particularly to 2-methylene-19-nor-20(S)-25-methyl-1α-hydroxycalciferol and its pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Recently, a new class of vitamin D analogs has been discovered, i.e. the so called 19-nor-vitamin D compounds, which are characterized by the replacement of the A-ring exocyclic methylene group (carbon 19), typical of the vitamin D system, by two hydrogen atoms.

Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)).

Recently, 2-substituted analogs of 1α,25-dihydroxy-19-norvitamin $D_3$ have also been synthesized, i.e. compounds substituted at 2-position with hydroxy or alkoxy groups (DeLuca et al., U.S. Pat. No. 5,536,713), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, their analogs which are characterized by the presence of an alkylidene (particularly methylene) substituent at the carbon 2 (C-2), i.e. 2-alkylidene-19-nor-vitamin D compounds, have now been synthesized and tested. Of particular interest are the analogs which are characterized by the transposition of the ring A exocyclic methylene group, present in the normal vitamin D skeleton, from carbon 10 (C-10) to carbon 2 (C-2), i.e. 2-methylene-19-nor-vitamin D compounds. Such vitamin D analogs seemed interesting targets because the relatively small alkylidene (particularly methylene) group at C-2 should not interfere with binding to the vitamin D receptor. Moreover, molecular mechanics studies performed on the model 1α-hydroxy-2-methylene-19-nor-vitamins indicate that such molecular modification does not change substantially the conformation of the cyclohexanediol ring A. However, introduction of the 2-methylene group into 19-nor-vitamin D carbon skeleton changes the character of its 1α- and 3β-A-ring hydroxyls. They are both now in the allylic positions, similarly, as 1α-hydroxyl group (crucial for biological activity) in the molecule of the natural hormone, 1α,25-$(OH)_2D_3$.

SUMMARY OF THE INVENTION

The present invention is directed toward 2-methylene-19-nor-20(S)-25-methyl-1α-hydroxycalciferol, its biological activity, and various pharmaceutical uses for this compound (hereinafter referred to as "TMM"). Unlike 2-methylene-19-nor-(20S)-1α,25-dihydroxycholecalciferol, TMM does not have a 25-hydroxyl and unlike 2-methylene-19-nor-(20S)-1α-hydroxycholecalciferol, TMM cannot be 25-hydroxylated in vivo because of the presence of a 25-methyl group.

Structurally this 19-nor analog is characterized by the general formula I shown below:

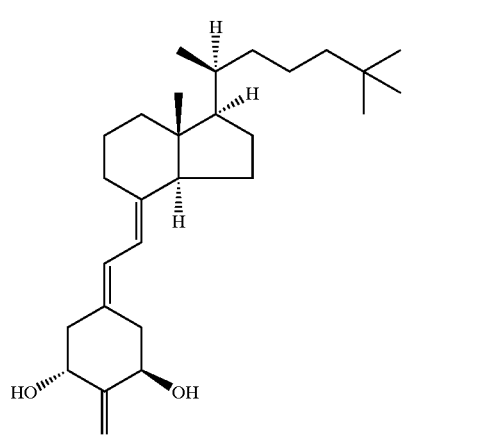

I

The above novel compound exhibits a desired, and highly advantageous, pattern of biological activity. This compound is characterized by relatively high intestinal calcium transport activity, as compared to that of 1α,25-dihydroxyvitamin $D_3$, while also exhibiting relatively low activity, as compared to 1α,25-dihydroxyvitamin $D_3$, in its ability to mobilize calcium from bone. Hence, this compound is highly specific in its calcemic activity. Its preferential intestinal calcium transport activity allows the in vivo administration of this compound for the treatment of metabolic bone diseases where bone loss is a major concern. Because of its intestinal calcemic activity, this compound would be a preferred therapeutic agent for the treatment of diseases where bone formation is desired, such as osteoporosis, especially low bone turnover osteoporsis, steroid induced osteoporosis, senile osteoporosis or postmenopausal osteoporosis, as well as osteomalacia and renal osteodystrophy. The treatment may be transdermal, oral or parenteral. The compounds may be present in a composition in an amount from about 0.01 µg/gm to about 100 µg/gm of the composition, preferably from about 0.1 µg/gm to about 50 µg/gm of the composition, and may be administered in dosages of from about 0.01 µg/day to about 100 µg/day, preferably from about 0.1 µg/day to about 50 µg/day.

The compound of the invention is also especially suited for treatment and prophylaxis of human disorders which are characterized by an imbalance in the immune system, e.g. in autoimmune diseases, including multiple sclerosis, diabetes mellitus, host versus graft reaction, and rejection of transplants; and additionally for the treatment of inflammatory diseases, such as rheumatoid arthritis, asthma, and inflammatory bowel diseases such as celiac disease and Crohn's disease as well as the improvement of bone fracture healing and improved bone grafts. Acne, alopecia, skin conditions such as dry skin (lack of dermal hydration), undue skin slackness (insufficient skin firmness), insufficient sebum secretion and wrinkles, and hypertension are other conditions which may be treated with the compound of the invention.

The above compound is also characterized by high cell differentiation activity. Thus, this compound also provides a therapeutic agent for the treatment of psoriasis, or as an anti-cancer agent, especially against leukemia, colon cancer, breast cancer and prostate cancer. The compound may be present in a composition to treat psoriasis and/or cancer in an amount from about 0.01 µg/gm to about 100 µg/gm of the composition, and may be administered topically, transdermally, orally or parenterally in dosages of from about 0.01 µg/day to about 100 µg/day.

This invention also provides a novel synthesis for the production of the end product of structure I, as well as a novel ketone intermediate formed during the synthesis.

DETAILED DESCRIPTION OF THE INVENTION

Figure 1:
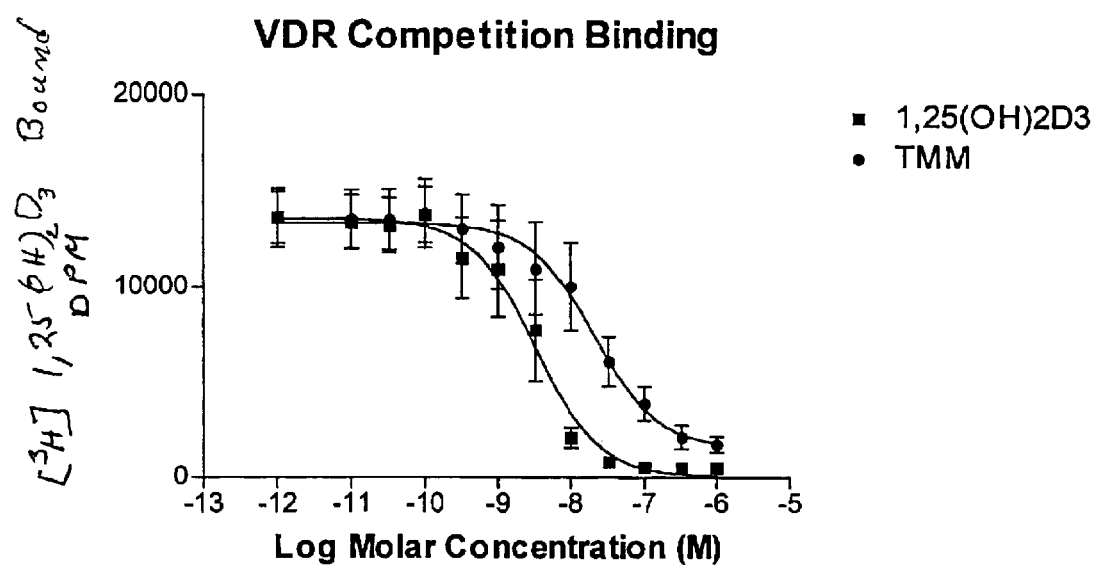
FIG. 1 is a graph illustrating the relative activity of 2-methylene-19-nor-20(S)-25-methyl-1α-hydroxycalciferol or 1α,25-dihydroxyvitamin $D_3$ to compete for binding of [3H]-1,25-$(OH)_2$—$D_3$ to the vitamin D pig intestinal nuclear receptor.

As used in the description and in the claims, the term "hydroxy-protecting group' signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

The preparation of 2-methylene-19-nor-20(S)-25-methyl-1α-hydroxycalciferol, having the basic structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1 and C-3 in the latter compound:

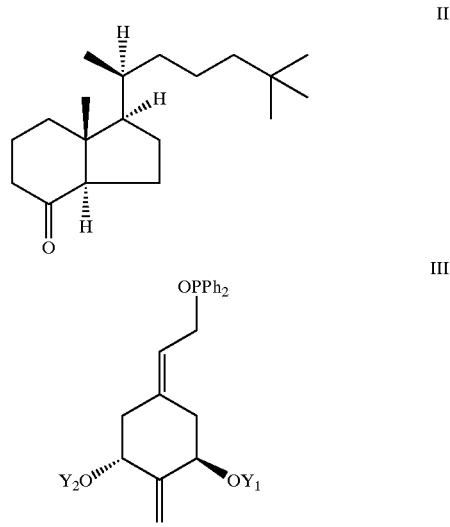

-continued

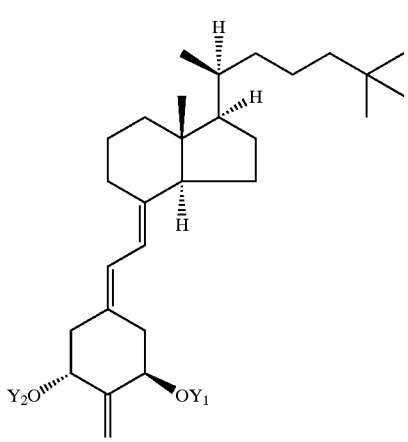

IV

In the structures III and IV groups $Y_1$ and $Y_2$ are preferably hydroxy-protecting groups, it being also understood that any functionalities that might be sensitive, or that interfere with the condensation reaction, be suitable protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

Hydrindanones of the general structure II can be prepared by known methods. One specific method begins with the ozonation of vitamin $D_2$, and is described and illustrated herein with reference to Schemes 1 and 2.

For the preparation of the required phosphine oxides of general structure III, a new synthetic route has been developed starting from methyl quinicate derivative, easily obtained from commercial (1R,3R,4S,5R)-(−)-quinic acid as described by Perlman et al., Tetrahedron Lett. 32, 7663 (1991) and DeLuca et al., U.S. Pat. No. 5,086,191. The overall process of transformation of the starting methyl ester into the desired A-ring synthons, is summarized in detail in these two references and the disclosure of such synthesis in U.S. Pat. No. 5,086,191 is specifically incorporated herein by reference. The final step in the synthesis will typically be hydrolysis of the hydroxy-protecting groups to give 2-methylene-19-nor-20(S)-25-methyl-1α-hydroxycalciferol (TMM).

This invention is described by the following illustrative examples. In these examples specific products identified by Arabic numerals (e.g. 1, 2, 3, etc) refer to the specific structures so identified in the preceding description and in SCHEME 1, SCHEME 2 and SCHEME 3. Reference should be made to SCHEMES 1 and 2 for EXAMPLE 1, and to SCHEME 3 for EXAMPLE 2.

EXAMPLE 1

Preparation of (20S)-de-A,B-8β-(tert-butyldimethylsilyl)oxy-20-(hydroxymethyl)pregnane (2)

Ozone was passed through a solution of vitamin $D_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate (3×80 mL) and the combined organic phase was washed with 1M aq. HCl, saturated aq. $NaHCO_3$, dried ($Na_2SO_4$) and concentrated under reduced pressure. The residue was chromatographed on silica gel with hexane/ethyl acetate (75:25) to give (20S)-de-A,B-20-(hydroxymethyl)pregnan-8β-ol 1 (1.21 g, 75% yield) as white crystals.

tert-Butyldimethylsilyl trifluoromethanesulfonate (3.24 mL, 3.72 g, 14.1 mmol) was added to a solution of the 8β,20-diol 1 (1 g, 4.7 mmol) and 2,6-lutidine (1.64 mL, 1.51 g, 14.1 mmol) in anhydrous DMF (15 mL) at 0° C. The mixture was stirred under argon at 0° C. for 1 h and then at room temperature for 18 h. The reaction was quenched with water (50 mL) and extracted with ethyl acetate (3×30 mL). The combined organic phase was washed with brine, dried ($Na_2SO_4$) and concentrated under reduced pressure. The residue was dissolved in anhydrous THF (8 mL), triethylamine (3 mL, 2.17 g, 21.5 mmol) and a solution of tetrabutylammonium fluoride (1 M in THF, 6.5 mL, 6.5 mmol) were added, followed by freshly activated molecular sieves 4A (3 g). The reaction mixture was stirred under argon at room temperature for 4 h, then filtered through a short layer of Celite and evaporated. The residue was dissolved in ethyl acetate (30 mL), washed with brine, water, dried ($Na_2SO_4$) and concentrated under reduced pressure. The pure alcohol 2 (1.42 g, 93% yield) was isolated by a chromatography on silica gel with hexane/ethyl acetate (97.5:2.5→95:5), as a colorless oil: $^1H$ NMR (500 MHz, $CDCl_3$) δ 4.00 (1H, d, J=2.4 Hz, 8α-H), 3.63 (1H, dd, J=10.5, 3.2 Hz, 22-H), 3.39 (1H, dd, J=10.5, 6.8 Hz, 22-H), 1.94 (1H, br.d, J=12.5 Hz), 1.02 (3H, d, J=6.6 Hz, 21-$H_3$), 0.924 (3H, s, 18-$H_3$), 0.882 (9H, s, Si-t-Bu), 0.005 and −0.010 (each 3H, each s, each Si-Me); $^{13}C$ NMR (125 MHz) δ 69.29 (d, C-8), 67.94 (t, C-22), 53.06 (d), 52.80 (d), 42.12 (s, C-13), 40.54 (t), 38.27 (d), 34.39 (t), 26.79 (t), 25.79 (q, Si$\underline{C}Me_3$), −23.08 (t), 18.00 (s, Si$\underline{C}Me_3$), 17.61 (t), 16.65 (q, C-2$\overline{1}$), 13.75 (q, C-18), −4.81 and −5.18 (each q, each Si$\underline{Me}$).

Preparation of (20S)-de-A,B-8β-(tert-butyldimethylsilyl)oxy-20-formylpregnane (3)

Sulfur trioxide pyridine complex (1.32 g, 8.28 mmol) was added to a solution of the alcohol 2 (451 mg, 1.38 mmol), triethylamine (960 μL, 697 mg, 6.9 mmol) in anhydrous methylene chloride (20 mL) and anhydrous DMSO (5 mL) at 0° C. The reaction mixture was stirred under argon at 0° C. for 20 min. and then concentrated. The residue was purified by column chromatography on silica gel with hexane/ethyl acetate (95:5) to give the aldehyde 3 (364 mg, 81% yield) as an oil: $^1H$ NMR (500 MHz, $CDCl_3$) δ 9.55 (1H, d, J=3.1 Hz, CHO), 4.00 (1H, s, 8α-H), 2.33 (1H, m, 20-H), 1.89 (1H, dm, J=12.4 Hz), 1.07 (3H, d, J=6.8 Hz, 21-$H_3$), 0.939 (3H, s, 18-$H_3$), 0.862 (9H, s, Si-t-Bu), −0.009 and −0.026 (each 3H, each s, each SiMe); $^{13}C$ NMR (125 MHz) δ 205.37 (d, CHO), 68.99 (d, C-8), 52.28 (d), 51.58 (d), 49.15 (d), 42.58 (s, C-13), 40.35 (t), 34.29 (t), 26.16 (t), 25.74 (q, Si$\underline{C}Me_3$), 23.27 (t), 17.96 (s, Si$\underline{C}Me_3$), 17.52 (t), 14.04 (q, C-2$\overline{1}$), 13.28 (q, C-18), −4.85 and −5.23 (each q, each Si$\underline{Me}$).

Preparation of (20R)-de-A,B-8β-(tert-butyldimethylsilyl)oxy-20-(hydroxymethyl)pregnane (4)

The aldehyde 3 (364 mg, 1.12 mmol) was dissolved in methylene chloride (15 mL) and a 40% aq. n-Bu$_4$NOH solution (1.47 mL, 1.45 g, 2.24 mmol) was added. The resulting mixture was stirred under argon at room temperature for 16 h, diluted with methylene chloride (20 mL), washed with water, dried (Na$_2$SO$_4$) and concentrated under reduced pressure. A residue was chromatographed on silica gel with hexane/ethyl acetate (95:5) to afford a mixture of aldehyde 3 and its 20-epimer (292 mg, 80% yield) in ca. 1:2 ratio (by $^1$H NMR).

This mixture of aldehydes (292 mg, 0.9 mmol) was dissolved in THF (5 mL) and NaBH$_4$ (64 mg, 1.7 mmol) was added, followed by a dropwise addition of ethanol (5 mL). The reaction mixture was stirred at room temperature for 30 min and it was quenched with a saturated aq. NH$_4$Cl solution. The mixture was extracted with ether (3×20 mL) and the combined organic phase was washed with water, dried (Na$_2$SO$_4$) and concentrated under reduced pressure. The residue was chromatographed on silica gel with hexane/ethyl acetate (96:4→80:20) to give the desired, pure (20R)-alcohol 4 (160 mg, 55% yield) as an oil and a mixture of 4 and its 20-epimer 2 (126 mg, 43% yield) in ca. 1:3 ratio (by $^1$H NMR).

$^1$H NMR (500 MHz, CDCl$_3$) δ 4.00 (1H, d, J=1.9 Hz, 8α-H), 3.70 (1H, dd, J=10.6, 3.2 Hz, 22-H), 3.43 (1H, dd, J=10.6, 7.0 Hz, 22-H), 0.94 (3H, d, J=6.7 Hz, 21-H$_3$), 0.927 (3H, s, 18-H$_3$), 0.884 (9H, s, Si-t-Bu), 0.007 and −0.006 (each 3H, each s, SiMe); $^{13}$C NMR (125 MHz) δ 69.30 (d, C-8), 66.83 (t, C-22), 53.02 (d), 52.96 (d), 41.91 (s, C-13), 40.12 (t), 37.48 (d), 34.38 (t), 26.71 (t), 25.79 (q, SiCMe$_3$), 22.85 (t), 18.01 (s, Si$\underline{C}$Me$_3$), 17.64 (t), 16.58 (q, $\overline{C-21}$), 14.07 (q, C-18), −4.81 and −5.18 (each q, each Si$\underline{Me}$).

Preparation of (20R)-de-A,B-8β-(tert-butyldimethylsilyl)oxy-20-[(p-toluenesulfonyl)oxymethyl]pregnane (5)

To a stirred solution of the alcohol 4 (134 mg, 0.41 mmol), 4-dimethylaminopyridine (10 mg, 0.08 mmol) and triethylamine (258 μL, 187 mg, 1.85 mmol) in anhydrous methylene chloride (6 mL) p-toluenesulfonyl chloride (118 mg, 0.62 mmol) was added at 0° C. The reaction mixture was allowed to warm to room temperature (4 h) and stirring was continued for additional 22 h. Methylene chloride (20 mL) was added and the mixture was washed with a saturated aq. NaHCO$_3$ solution, dried (Na$_2$SO$_4$) and concentrated under reduced pressure. A residue was chromatographed on silica gel with hexane/ethyl acetate (95:5) to afford a tosylate 5 (192 mg, 98% yield) as a colorless oil: [α]$_D$+15.7° (c 1.0, CHCl$_3$); $^1$H NMR (500 MHz, CDCl$_3$) δ 7.78 (2H, d, J=8.2 Hz, o-H$_{Ts}$), 7.33 (2H, d, J=8.2 Hz, m-H$_{Ts}$), 4.11 (1H, dd, J=9.3, 3.4 Hz, 22-H), 3.96 (1H, d, J=2.1 Hz, 8α-H), 3.77 (1H, dd, J=9.3, 7.4 Hz, 22-H), 2.443 (3H, s, Me$_{Ts}$), 0.87 (3H, d, J=6.5 Hz, 21-H$_3$), 0.864 (9H, s, Si-t-Bu), 0.810 (3H, s, 18-H$_3$), −0.009 and −0.027 (each 3H, each s, each SiMe); $^{13}$C NMR (125 MHz) δ 144.55 (s, p-C$_{Ts}$), 133.06 (s, i-C$_{Ts}$), 129.70 (d, m-C$_{Ts}$), 127.91 (d, o-C$_{Ts}$), 74.26 (t, C-22), 69.09 (d, C-8), 52.65 (d), 52.51 (d), 41.72 (s, C-13), 39.83 (t), 34.65 (d), 34.16 (t), 26.60 (t), 25.74 (q, SiCMe$_3$), 22.65 (t), 21.61 (q, Me$_{Ts}$), 17.86 (s, Si$\underline{C}$Me$_3$), 17.48 (t), 16.65 (q, C-21), 13.99 (q, C-18), −4.86 and −5.23 (each q, each Si$\underline{Me}$); MS (EI) m/z no M$^+$, 437 (2, M$^+$-C$_3$H$_7$), 423 (1 M$^+$-C$_4$H$_9$), 348 (2, M$^+$-t-BuMe$_2$SiOH), 309 (2, M$^+$-OSO$_2$C$_6$H$_4$CH$_3$), 229 (76), 177 (100, M$^+$-t-BuMe$_2$SiOH—OSO$_2$C$_6$H$_4$CH$_3$), 135 (33), 121 (38), 107 (27), 95 (41); exact mass calculated for C$_{22}$H$_{35}$O$_4$SSi (M$^+$-C$_4$H$_9$) 423.2025, found 423.2036.

Preparation of (20S)-de-A,B-8β-(tert-butyldimethylsilyl)oxy-25-methylcholestane (8)

Magnesium turnings (0.53 g, 22 mmol), 1-chloro-3,3-dimethylbutane 6 (1.32 g, 11 mmol) and iodine (2 crystals) were refluxed in anhydrous THF (15 mL) for 6 h. The solution of the formed Grignard reagent 7 was cooled to −78° C. and added dropwise via cannula to a solution of the tosylate 5 (183 mg, 0.38 mmol) in anhydrous THF (3 mL) at −78° C. Then 6 mL of the solution of Li$_2$CuCl$_4$ [prepared by dissolving of a dry LiCl (232 mg, 5.46 mmol) and dry CuCl$_2$ (368 mg, 2.75 mmol) in anhydrous THF (27 mL)] was added dropwise via cannula to the reaction mixture at −78° C. The cooling bath was removed and the mixture was stirred at room temperature for 20 h and then poured into 1M aq. H$_2$SO$_4$ solution (25 mL) containing ice (ca. 100 g). The mixture was extracted with methylene chloride (3×50 mL) and the combined organic layers were washed with saturated aq. NH$_4$Cl, saturated aq. NaHCO$_3$, dried (Na$_2$SO$_4$) and concentrated under reduced pressure. The residue was chromatographed on silica gel with hexane to give the product 8 (130 mg, 87% yield) as a colorless oil: [α]$_D$+19.9° (c 2.2, CHCl$_3$); $^1$H NMR (500 MHz, CDCl$_3$) δ 4.00 (1H, d, J=1.5 Hz, 8α-H), 1.94 (1H, dm, J=12.5 Hz), 0.915 (3H, s, 18-H$_3$), 0.891 (9H, S, Si-t-Bu), 0.866 (9H, s, 25-Me$_3$), 0.81 (3H, d, J=6.5 Hz, 21-H$_3$), 0.010 and −0.002 (each 3H, each s, each SiMe); $^{13}$C NMR (125 MHz) δ 69.52 (d, C-8), 56.46 (d), 53.17 (d), 44.57 (t), 42.20 (s, C-13), 40.68 (t), 36.17 (t), 34.82 (d), 34.51 (t), 30.36 (s, C-25), 29.47 (q, 25-$\underline{Me}_3$), 27.27 (t), 25.82 (q, SiCMe$_3$), 23.01 (t), 20.99 (t), 18.60 (q, C-21), 18.03 (s, Si$\underline{C}$Me$_3$), 17.76 (t), 14.00 (q, C-18), −4.78 and −5.15 (each q, each Si$\underline{Me}$); MS (EI) m/z no M$^+$, 379 (11, M$^+$-CH$_3$), 351 (3, M$^+$-), 337 (72), 319 (2), 292 (10), 264 (66), 247 (10), 159 (17), 135 (27), 75 (100); exact mass calculated for C$_{24}$H$_{47}$OSi (M$^+$-CH$_3$) 379.3396, found 379.3398.

Preparation of (20S)-de-A,B-25-methylcholestan-8β-ol (9)

The protected alcohol 8 (100 mg, 254 μmol) was dissolved in anhydrous methanol (5 mL) and hydrogen fluoride-pyridine (2.5 mL) was added. The mixture was stirred under argon at room temperature for 3 days, then ethyl acetate (20 mL) was added. The organic phase was washed with brine and water, dried (Na$_2$SO$_4$) and concentrated under reduced pressure. The residue was diluted with hexane and chromatographed on silica gel with hexane to recover the substrate 8 (16 mg). Elution with hexane/ethyl acetate (8:2) gave the pure alcohol 9 (58 mg, 82% yield), as a colorless oil: [α]$_D$+8.2° (c 1.15, CHCl$_3$); $^1$H NMR (500 MHz, CDCl$_3$) δ 4.07 (1H, s, 8α-H), 1.98 (1H, dm, J=12.2 Hz), 0.928 (3H, s, 18-H$_3$), 0.861 (9H, s, 25-Me$_3$), 0.82 (3H, d, J=6.5 Hz, 21-H$_3$); $^{13}$C NMR (125 MHz) δ 69.46 (d, C-8), 56.32 (d), 52.68 (d), 44.56 (t), 41.89 (s, C-13), 40.31 (t), 36.09 (t), 34.82 (d), 33.59 (t), 30.35 (s, C-25), 29.45 (q, 25-Me$_3$), 27.12 (t), 22.43 (t), 20.96 (t), 18.54 (q, C-21), 17.50 (t), 13.74 (q, C-18); MS (EI) m/z 280 (34, M$^+$), 265 (15, M$^+$-Me), 247 (18), 237 (1), 166 (28), 135 (30), 111 (100), 97 (37), 81 (23); exact mass calculated for C$_{19}$H$_{36}$O (M$^+$) 280.2766, found 280.2753.

Preparation of (20S)-de-A,B-25-methylcholestan-8-one (II)

Pyridinium dichromate (102 mg, 271 μmol) was added to a solution of the alcohol 9 (19 mg, 68 μmol) and pyridinium p-toluenesulfonate (2 mg, 8 μmol) in anhydrous methylene chloride (6 mL). The resulting suspension was stirred at room temperature for 4 h. The reaction mixture was filtered through a Waters silica Sep-Pak cartridge (2 g) that was further washed with hexane/ethyl acetate (8:2). After removal of solvents ketone II (16 mg, 85% yield) was obtained as a colorless oil: $^1$H NMR (500 MHz, CDCl$_3$) δ 2.45 (1H, dd, J=11.5, 7.7 Hz), 0.875 (9H, s, 25-Me$_3$), 0.86 (3H, d, J=5.9 Hz, 21-H$_3$), 0.638 (3H, s, 18-H$_3$); $^{13}$C NMR (125 MHz) δ 212.18 (C-8), 62.06, 56.25, 49.95 (C-13), 44.52, 40.96, 38.85, 36.30, 34.90, 30.35 (C-25), 29.42 (25-Me$_3$), 27.21, 24.06, 20.89, 18.95 (C-21), 18.49, 12.68 (C-18); MS (EI) m/z 278 (66, M$^+$), 263 (79, M$^+$-Me), 245 (10, M$^+$-Me-H$_2$O), 235 (84, M$^+$-Me-CO), 179 (12, M$^+$-C$_7$H$_{15}$), 166 (25), 152 (49, M$^+$-C$_9$H$_{18}$), 124 (100, M$^+$-CO—C$_9$H$_{18}$), 111 (96), 96 (42), 81 (30); exact mass calculated for C$_{19}$H$_{34}$O 278.2610, found 278.2606.

EXAMPLE 2

Preparation of (20S)-2-methylene-19-nor-25-methyl-1α-hydroxycalciferol (I)

To a solution of phosphine oxide 10 (45 mg, 77 μmol) in anhydrous THF (500 μL) at −20° C. was slowly added PhLi (1.56 M in cyclohexane-ether, 100 μL, 156 μmol) under argon with stirring. The solution turned deep orange. After 30 min the mixture was cooled to −78° C. and a precooled (−78° C.) solution of ketone II (17 mg, 61 μmol) in anhydrous THF (200+100 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 11 (24 mg). The Sep-Pak was then washed with hexane/ethyl acetate (96:4) to recover the unchanged C,D-ring ketone II (4 mg), and with ethyl acetate to recover diphenylphosphine oxide 10 (21 mg). The protected vitamin 11 was further purified by HPLC (10×250 mm Zorbax-Silica column, 4 mL/min) using hexane/2-propanol (99.9:0.1) solvent system. Pure compound II (19.9 mg, 51% yield) was eluted at R$_V$=15 mL as a colorless oil: UV (in hexane) λ$_{max}$ 262.2, 252.2, 243.3 nm; $^1$H NMR (500 MHz, CDCl$_3$) δ 6.22 and 5.83 (1H and 1H, each d, J=11.2 Hz, 6- and 7-H), 4.97 and 4.92 (1H and 1H, each s, =CH$_2$), 4.41 (2H, m, 1β- and 3α-H), 2.82 (1H, br. d, J=12.3 Hz, 9β-H), 2.53 (1H dd, J=13.2, 5.8 Hz, 10α-H), 2.46 (1H, dd, J=12.7, 4.6 Hz, 4α-H), 2.31 (1H, dd, J=13.2, 2.9 Hz, 10β-H), 2.17 (1H, dd, J=12.7, 8.3 Hz, 4β-H), 2.30–1.93 (2H, m), 1.90–1.80 (1H, m), 0.891 (9H, s, Si-t-Bu), 0.862 (9H, s, 25-Me$_3$), 0.856 (9H, s, Si-t-Bu), 0.84 (3H, d, J=6.4 Hz, 21-H$_3$), 0.535 (3H, s, 18-H$_3$), 0.076, 0.061, 0.046 and 0.019 (each 3H, each s, 4×Si—CH$_3$); $^{13}$C NMR (125 MHz) δ 152.93 (s, C-2), 141.32 (s, C-8), 132.68 (s, C-5), 122.42 (d, C-6), 116.04 (d, C-7), 106.27 (t, =CH$_2$), 72.52 and 71.59 (each d, C-1 and C-3), 56.34 (d), 56.17 (d), 47.59 (t), 45.70 (s, C-13), 44.57 (t), 40.47 (t), 38.51 (t), 36.34 (t), 35.61 (d), 30.39 (s, C-25), 29.48 (q, 25-Me$_3$), 28.76 (t), 27.56 (t), 25.85 (q, SiCMe$_3$), 25.79 (q, SiCMe$_3$), 23.48 (t), 22.12 (t), 20.93 (t), 18.65 (q, C-21), 18.28 (s, SiCMe$_3$), 18.18 (s, SiCMe$_3$), 12.31 (q, C-18), −4.81, −4.87, −5.05 and −5.14 (each q, each SiMe); MS (EI) m/z 642 (8, M$^+$), 627 (3, M$^+$-Me), 585 (6, M$^+$-C$_4$H$_9$), 510 (100, M$^+$-t-BuMe$_2$SiOH), 495 (5, M$^+$-t-BuMe$_2$SiOH-Me), 453 (3), 366 (24), 257 (7), 234 (9), 197 (7), 147 (10), 73 (46); exact mass calculated for C$_{40}$H$_{74}$O$_2$Si$_2$ (M$^+$) 642.5227, found 642.5206.

Protected vitamin 11 (1.7 mg, 2.6 μmol) was dissolved in anhydrous THF (3 mL) and a solution of tetrabutylammonium fluoride (1 M in THF, 50 μL, 50 μmol) was added, followed by freshly activated molecular sieves 4A (300 mg). The mixture was stirred under argon at room temperature for 18 h, then diluted with 2 mL of hexane/ethyl acetate (6:4) and applied on a Waters silica Sep-Pak cartridge (2 g). Elution with the same solvent system gave the crude product I that was further purified by HPLC (10×250 mm Zorbax-Silica column, 4 mL/min) using hexane/2-propanol (9:1) solvent system. Analytically pure 2-methylene-19-norvitamin I (768 μg, 71% yield) was collected at R$_V$=26 mL as a colorless oil: UV (in EtOH) λ$_{max}$ 261.2, 251.3, 243.1 nm; $^1$H NMR (500 MHz, CDCl$_3$) δ 6.36 and 5.89 (1H and 1H, each d, J=11.3 Hz, 6- and 7-H), 5.11 and 5.09 (each 1H, each s, =CH2), 4.48 (2H, m, 1β- and 3α-H), 2.85 (1H, dd, J=13.3, 4.7 Hz, 10β-H), 2.82 (1H, br d, J=13.0 Hz, 9β-H), 2.57 (1H, dd, J=13.3, 3.8 Hz, 4α-H), 2.33 (1H, dd, J=13.3, 6.2 Hz, 4β-H), 2.29 (1H, dd, J=13.3, 8.3 Hz, 10α-H), 2.05–1.95 (2H, m), 1.90–1.82 (1H, m), 0.866 (9H, s, 25-Me$_3$), 0.84 (3H, d, J=6.5 Hz, 21-H$_3$), 0.548 (3H, s, 18-H$_3$); MS (EI) m/z 414 (100, M$^+$), 399 (8, M$^+$-Me), 396 (5, M$^+$-H$_2$O), 381 (8, M$^+$-Me-H$_2$O), 363 (2, M$^+$-Me-2H$_2$O), 329 (28, M$^+$-C$_6$H$_{13}$), 287 (36, M$^+$-C$_9$H$_{19}$), 261 (24), 192 (14), 161 (19), 147 (37), 135 (51), 107 (42); exact mass calculated for C$_{28}$H$_{46}$O$_2$ 414.3498, found 414.3515.

BIOLOGICAL ACTIVITY OF 2-METHYLENE-19-NOR-20(S)-25-METHYL-1α-HYDROXYCALCIFEROL

Competitive binding of the analog to the porcine intestinal receptor was carried out by the method described by Dame et al (Biochemistry 25, 4523–4534, 1986).

The differentiation of HL-60 promyelocytes into monocytes was determined as described by Ostrem et al (J. Biol. Chem. 262, 14164–14171, 1987).

Competitive binding of 1α, 25-(OH)$_2$D$_3$ and the synthesized vitamin D analog to the porcine intestinal vitamin D receptor was carried out in triplicate on two different occasions. ED$_{50}$ values can be derived from dose-response curves (FIG. 1) and represent the analog concentration required for 50% displacement of the radiolabeled 1α,25-(OH)$_2$D$_3$ from the receptor protein. Binding ratio can then be determined from the ratio of the analog average ED$_{50}$ to the ED$_{50}$ for 1α,25-(OH)$_2$D$_3$.

Induction of differentiation of HL-60 promyelocytes to monocytes by 1α,25-(OH)$_2$D$_3$ and the synthesized vitamin D analog was determined by measuring the percentage of cells reducing nitro blue tetrazolium (NBT). The experiment was repeated three times. The values ED$_{50}$ can be derived from dose-response curves (FIG. 2) and represent the analog concentration capable of inducing 50% maturation. Differentiation activity ratio can then be determined from the ratio of the analog average ED$_{50}$ to the ED$_{50}$ for 1α,25-(OH)$_2$D$_3$.

EXAMPLE 3

Goal: Determine whether or not TMM has bone calcium mobilization activity and how it compares to 1,25(OH)$_2$D$_3$ and 2-methylene-19-nor-20(S)-1α, 25-(OH)$_2$D$_3$ (hereinafter referred to as 2MD).

Animals:

5–6 week old CD-1 mice were placed in the +D mouse room and fed chow diet. They were allowed to acclimate for 5 days before being switched to a purified diet described by Yang et al (Arch. Biochem. Biphys. 303, 98, 1993) containing 0.02% calcium and 0.3% P. Two days after the diet switch, dose administration began.

Experimental Design:

All animals were weighed prior to dosing. The animals were divided into groups containing 5 animals/group. All animals were administered the drug by oral gavage one time. The dose was delivered in 100 µl Neobee oil/25 g mouse. Blood (about 80 µl) was collected from the retroorbital sinus predose, and 24 h, 48 h, and 72 h post-dose and total serum calcium measured using atomic absorption spectrometry.

Group 1: Neobee oil
Group 2: 50 ug 1,25(OH)$_2$D$_3$/kg bw
Group 3: 450 ug 1,25(OH)$_2$D$_3$/kg bw
Group 4: 0.5 ug 2MD/kg bw
Group 5: 1.5 ug 2MD/kg bw
Group 6: 4.5 ug 2MD/kg bw
Group 7: 13.5 ug 2MD/kg bw
Group 8: 0.5 ug TMM/kg bw
Group 9: 1.5 ug TMM/kg bw
Group 10: 4.5 ug TMM/kg bw
Group 11: 13.5 ug TMM/kg bw Results:

Table 1 shows the rise in serum calcium of mice fed the 0.02% calcium diet and given either vehicle, vehicle plus 1α, 25(OH)$_2$D$_3$, vehicle plus 2MD, or vehicle plus TMM. The rise in serum calcium comes from bone mobilization only since no calcium is available from the intestine.

TABLE 1

Bone Calcium Mobilization Activity

| Compound | Dose Level | Bone Calcium Mobilization (mg/dL) | | | |
| --- | --- | --- | --- | --- | --- |
| | | 0 hr | 24 hr | 48 hr | 72 hr |
| Vehicle | | 8.4 ± 0.3 | 8.9 ± 0.1 | 9.3 ± 0.1 | 9.1 ± 0.1 |
| 1α,25(OH)$_2$D$_3$ | 50 µg/kg | 8.8 ± 0.2 | 10.9 ± 0.1 | 9.6 ± 0.3 | 9.1 ± 0.2 |
| | 450 µg/kg | 8.8 ± 0.2 | 11.6 ± 0.3 | 11.4 ± 0.7 | 9.4 ± 0.4 |
| 2-methylene-19-nor 1α,25(OH)$_2$D$_3$ (2MD) | 0.5 µg/kg | 8.8 ± 0.3 | 9.4 ± 0.2 | 9.2 ± 0.2 | 8.9 ± 0.2 |
| | 1.5 µg/kg | 8.8 ± 0.2 | 10.1 ± 0.1 | 10.5 ± 0.2 | 10.1 ± 0.2 |
| | 4.5 µg/kg | 8.8 ± 0.0 | 10.9 ± 0.2 | 12.6 ± 0.5 | 12.0 ± 0.4 |
| | 13.5 µg/kg | 8.6 ± 0.1 | 11.5 ± 0.4 | 10.8 ± 0.5 | 13.4 ± 0.6 |
| 2-methylene-19-nor-25-methyl-1α,25(OH)$_2$D$_3$ (TMM) | 0.5 µg/kg | 8.7 ± 0.2 | 8.8 ± 0.1 | 8.7 ± 0.1 | 8.7 ± 0.1 |
| | 1.5 µg/kg | 8.7 ± 0.2 | 8.7 ± 0.2 | 8.6 ± 0.1 | 8.9 ± 0.2 |
| | 4.5 µg/kg | 8.5 ± 0.3 | 9.0 ± 0.1 | 8.9 ± 0.1 | 8.8 ± 0.2 |
| | 13.5 µg/kg | 8.8 ± 0.1 | 9.7 ± 0.2 | 9.9 ± 0.3 | 9.5 ± 0.3 |

Mice fed a 0.02% calcium diet can only elevate their serum calcium levels by resorbing bone because no calcium is available through intestinal absorption. The data in Table 1 show that TMM only at the highest dose caused bone resorption in vivo. At lower doses, there was no significant elevation of serum calcium. In contrast, 1,25-(OH)$_2$D$_3$ was found effective at 50 µg/kg bw and 450 µg/kg bw. Thus, TMM is approximately equal to 1,25-(OH)$_2$D$_3$ in raising serum calcium but only one-tenth as active as 2MD in this regard. Thus, the importance of the 25-hydroxyl for bone calcium mobilization is illustrated.

Figure 3:
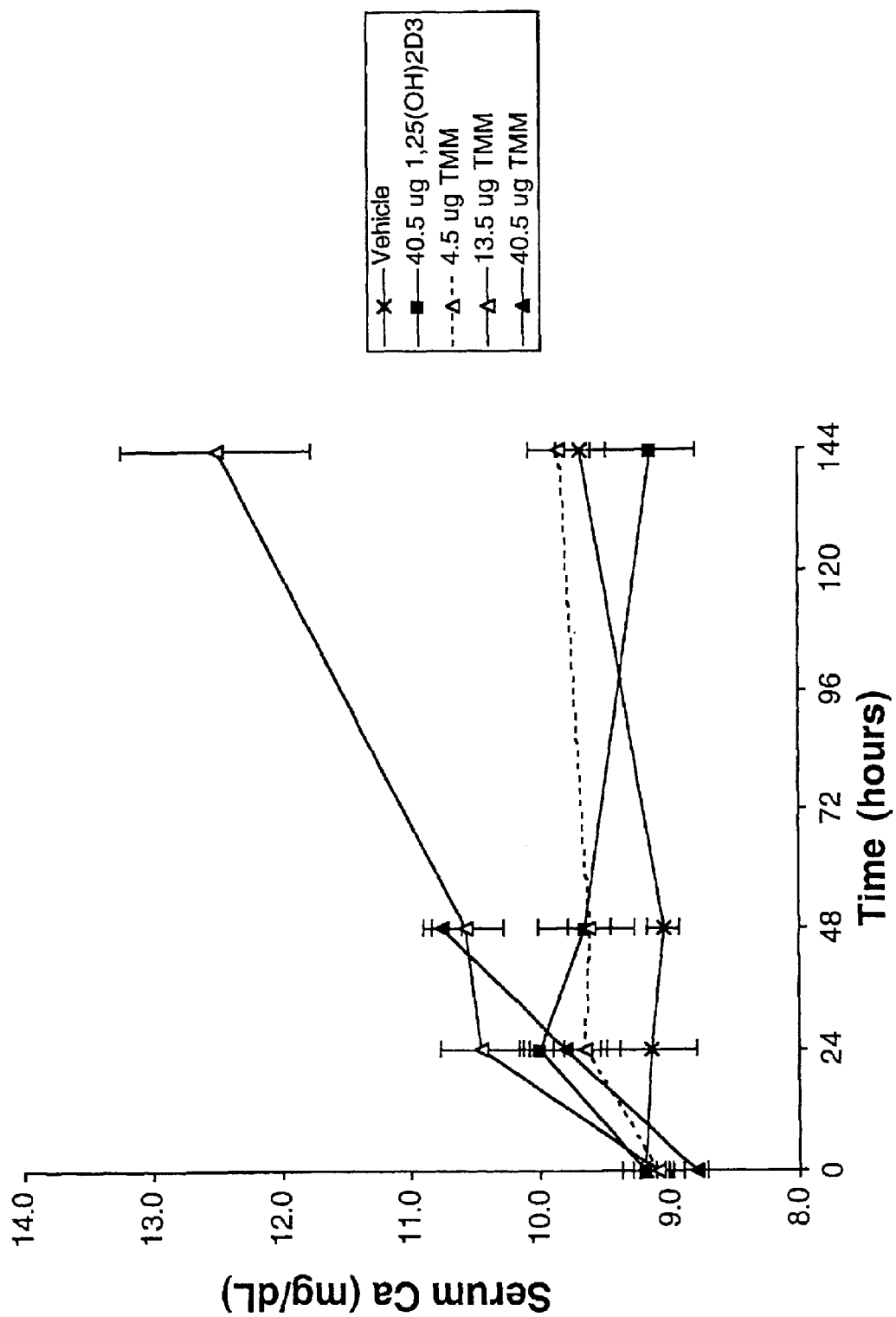
FIG. 3 is a graph illustrating serum calcium versus time of mice injected with vehicle plus alendronate, with 1α,25-dihydroxyvitamin $D_3$ plus alendronate, or with 2-methylene-19-nor-20(S)-25-methyl-1α-hydroxycalciferol (TMM) plus alendronate. Since alendronate blocks bone resorption the rise in serum calcium reflects only intestinal absorption.

FIG. 3 shows that TMM is more active than 1,25-(OH)$_2$D$_3$ in intestinal calcium absorption activity by a factor of about 10. In this measurement, alendronate is used to block bone resorption so the rise in serum calcium is because of increased calcium absorption from the intestine.

EXAMPLE 4

Goal: Determine whether or not TMM has intestinal calcium transport activity and how it compares to 1,25(OH)$_2$D$_3$.
Animals:

5–6 week old CD-1 mice were placed in the +D mouse room and fed chow diet. They were allowed to acclimate for 7 days before being switched to a diet containing 0.47% calcium.

Experimental Design:

All animals were weighed prior to dosing and divided into groups containing 5 animals/treatment group. Two-three animals were housed/cage. All animals were administered the vitamin D analog by oral gavage one time and the alendronate by intraperitoneal injection one time. The doses were delivered in 100 µl Neobee oil/25 g mouse (vitamin D analogs) and 100 ul PBS/mouse (alendronate). Alendronate was administered one day prior to the vitamin D analogs to allow it to work on the bone prior to administration of bone-active compounds. Blood (about 80 µl) was collected from the retroorbital sinus predose, and 24 h, 48 h, and 144 h post-dose. Once all time points were collected, the serum was diluted 1:50 in 0.1% Lanthum Chloride and analyzed by atomic absorption spectrometry for determination of total serum calcium levels.

Group 1: Neobee oil+Alendronate (1.75 mg/kg bw)
Group 2: 40.5 ug 1,25(OH)$_2$D$_3$/kg bw+Alendronate (1.75 mg/kg bw)
Group 3: 4.5 ug TMM/kg bw+Alendronate (1.75 mg/kg bw)
Group 4: 13.5 ug TMM/kg bw+Alendronate (1.75 mg/kg bw)
Group 5: 40.5 ug TMM/kg bw+Alendronate (1.75 mg/kg bw)

Results:

FIG. 3 illustrates that in contrast to bone calcium mobilization activity, TMM has more intestinal calcium transport activity than does 1,25(OH)$_2$D$_3$.

Figure 2:
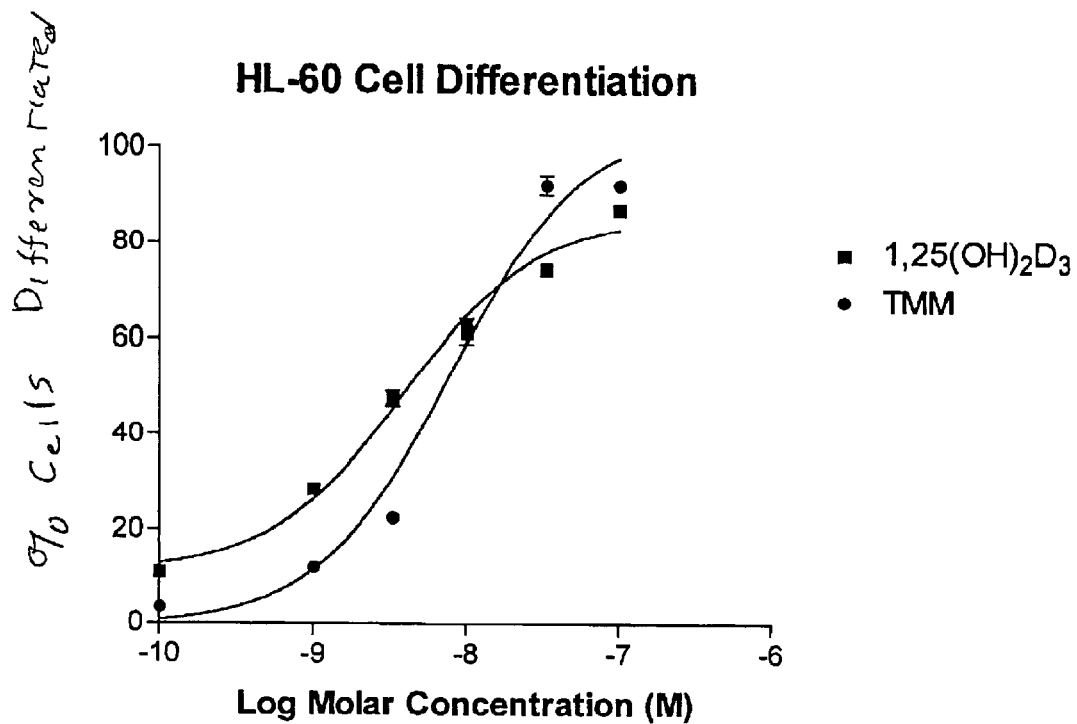
FIG. 2 is a graph illustrating the percent HL-60 cell differentiation as a function of the concentration of 2-methylene-19-nor-20(S)-25-methyl-1α-hydroxycalciferol or 1α,25-dihydroxyvitamin $D_3$.

The biological data in FIGS. 1–3 and Table 1 can be summarized as follows:

The binding of the 25-methyl derivative TMM to the recombinant rat vitamin D receptor illustrates that TMM binds one-tenth as well to the vitamin D receptor as the native hormone, 1,25-(OH)$_2$D$_3$. This is surprising because TMM lacks a 25-hydroxyl group. However, TMM, when tested in HL-60 differentiation, revealed activity essentially equal to that of 1,25-(OH)$_2$D$_3$. Thus, TMM is very potent even without a 25-hydroxyl group. Of great interest is the in vivo data obtained in CD-1 mice. The data on animals following a single dose of the compound at the indicated levels showed that TMM had very little bone calcium mobilization activity. Bone calcium mobilization (serum calcium level) was minimal even up to 13.5 micrograms of TMM/kg body weight. Thus, its activity not only fell far below 2-methylene-19-nor-20(S)-1α, 25-$(OH)_2D_3$ or 2MD but also below that of the native hormone, 1,25-$(OH)_2D_3$. Of considerable interest, however, is that TMM had a very strong effect on intestinal calcium absorption. The activity of TMM on intestinal calcium absorption is 10 times that of 1,25-$(OH)_2D_3$ which in previous work was shown to have about the same activity as 2-methylene-19-nor-20(S)-1α, 25-$(OH)_2D_3$. Thus, TMM shows selectivity for activity on the intestine, where utilization of environmental calcium is highly desirable without associated bone calcium mobilization. It could be used as a maintenance vitamin D compound in patients where bone loss due to bone mobilization is not desired. Such a circumstance could be any form of osteoporosis. The activity of TMM in causing cellular differentiation and suppression of HL-60 cell growth is also consistent with its use in the treatment of malignant disease or in the treatment of psoriasis, a hyperproliferation of keratinocyte disease of skin.

For treatment purposes, the novel compound of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compound may be administered orally, topically, parenterally or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 µg to 100 µg per day of the compound are appropriate for treatment purposes, such doses being adjusted according to the disease to be treated, its severity and the response of the subject as is well understood in the art. Since the new compound exhibits specificity of action, it may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of the 2-methylene-19-nor-vitamin D compound as defined by the above formula I as the active ingredient, and a suitable carrier. An effective amount of such compound for use in accordance with this invention is from about 0.01 µg to about 100 µg per gm of composition, and may be administered topically, transdermally, orally or parenterally in dosages of from about 0.01 µg/day to about 100 µg/day.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compound is advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

Scheme 1
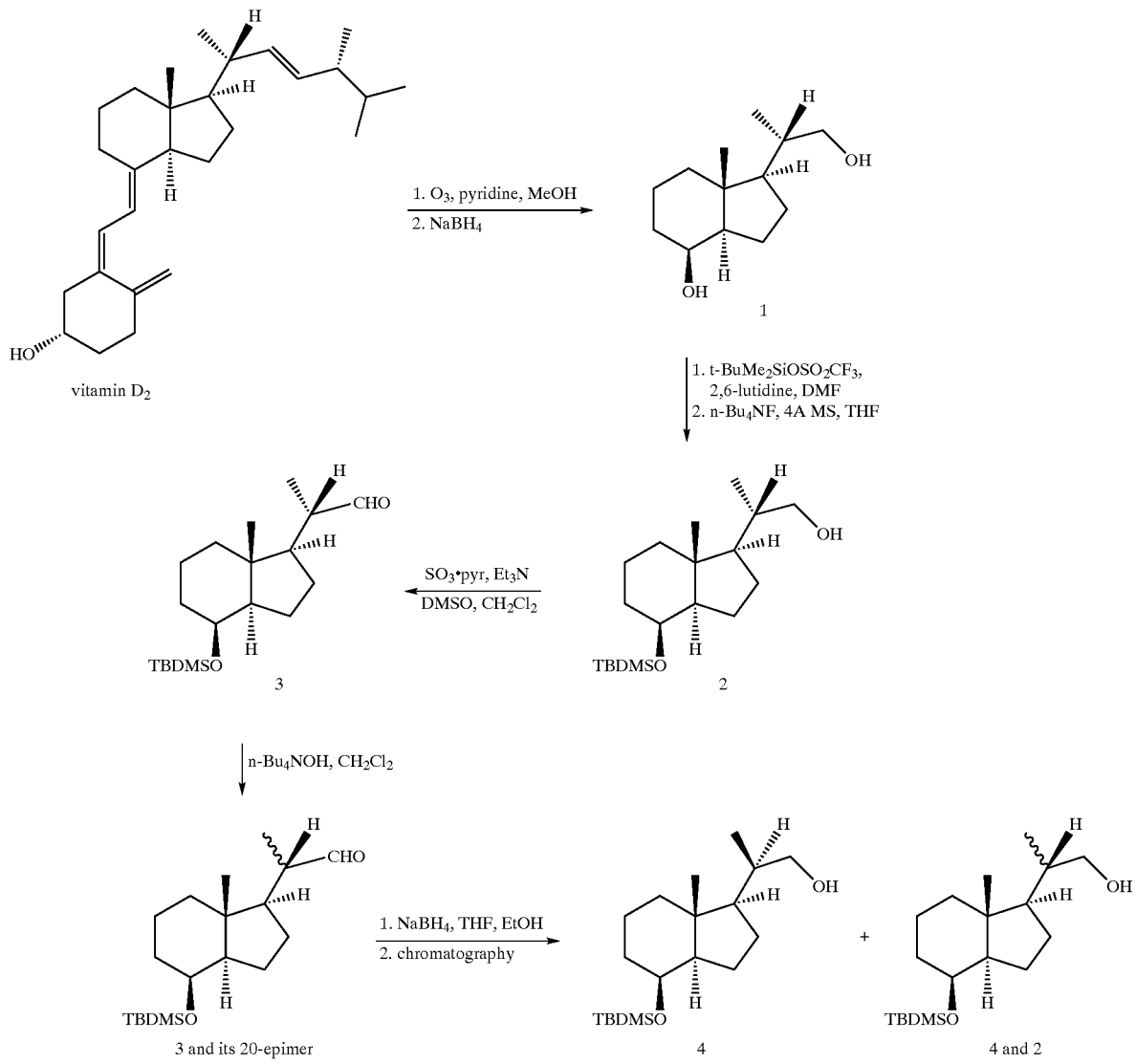
Scheme 2
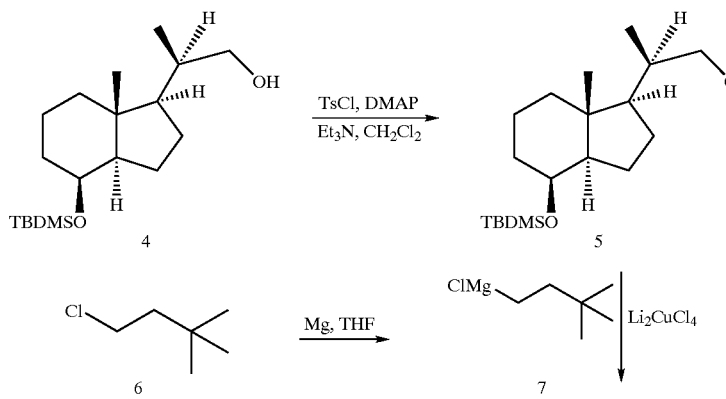

-continued
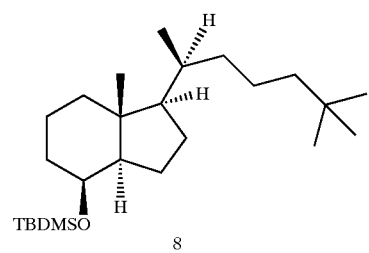
8
↓ HF·pyridine, MeOH
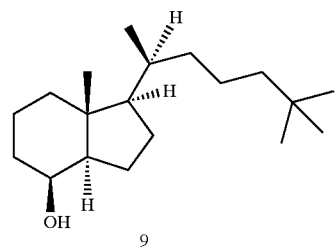
9
↓ PDC, PPTS, CH₂Cl₂
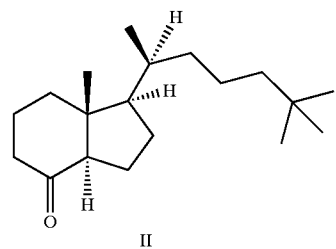
II
Scheme 3
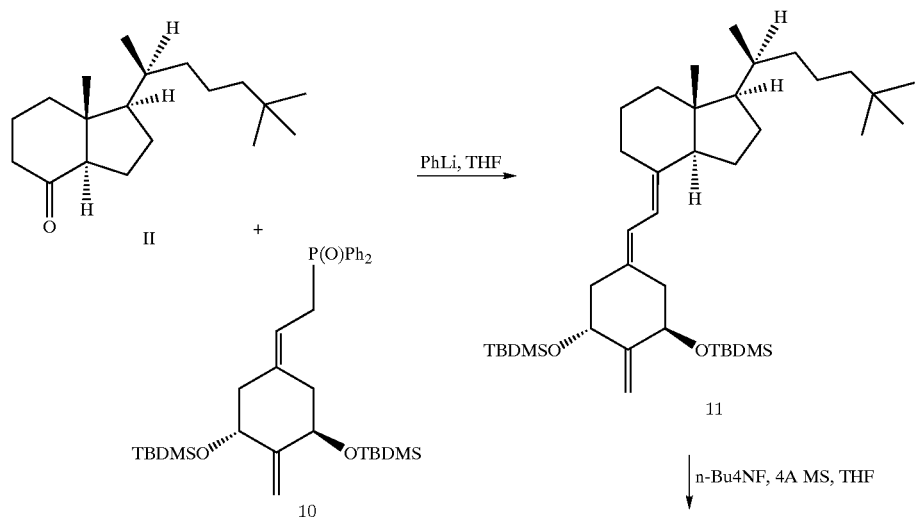
↓ n-Bu4NF, 4A MS, THF -continued

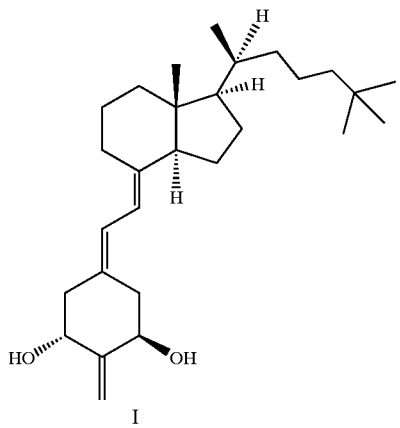

I

We claim:

1. A compound having the formula:

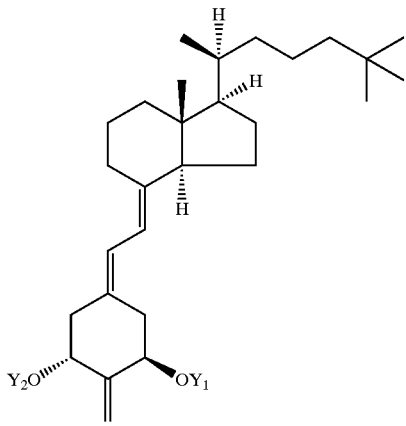

where $Y_1$ and $Y_2$, which may be the same or different, are each selected from the group consisting of hydrogen and a hydroxy-protecting group.

2. 2-methylene-19-nor-20(S)-25-methyl-1α-hydroxycalciferol.

3. A pharmaceutical composition containing at least one compound as claimed in claim 1 together with a pharmaceutically acceptable excipient.

4. The pharmaceutical composition of claim 3 containing 2-methylene-19-nor-20(S)-25-methyl-1α-hydroxycalciferol in an amount from about 0.01 μg to about 100 μg.

5. The pharmaceutical composition of claim 3 containing 2-methylene-19-nor-20(S)-25-methyl-1α-hydroxycalciferol in an amount from about 0.1 μg to about 50 μg.

6. A method of treating metabolic bone disease where it is desired to maintain or increase bone mass comprising administering to a patient with said disease an effective amount of a compound having the formula:

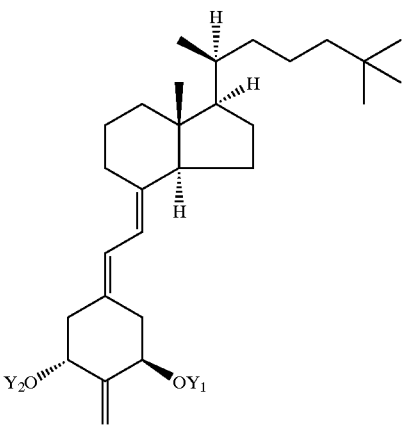

where $Y_1$ and $Y_2$, which may be the same or different, are each selected from the group consisting of hydrogen and a hydroxy-protecting group.

7. The method of claim 6 where the disease is senile osteoporosis.

8. The method of claim 6 where the disease is postmenopausal osteoporosis.

9. The method of claim 6 where the disease is steroid-induced osteoporosis.

10. The method of claim 6 where the disease is low bone turnover osteoporosis.

11. The method of claim 6 where the disease is osteomalacia.

12. The method of claim 6 where the disease is renal osteodystrophy.

13. The method of claim 6 wherein the compound is administered orally.

14. The method of claim 6 wherein the compound is administered parenterally.

15. The method of claim 6 wherein the compound is administered transdermally.

16. The method of claim 6 wherein the compound is administered in a dosage of from 0.01 μg to 100 μg per day.

17. The method of claim 6 wherein the compound is 2-methylene-19-nor-20(S)-25-methyl-1α-hydroxycalciferol.

18. A method of treating psoriasis comprising administering to a patient with said disease an effective amount of a compound having the formula:

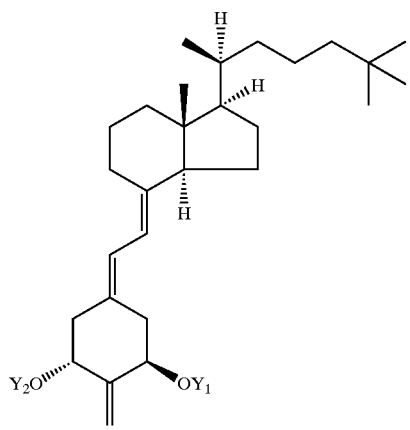

where $Y_1$ and $Y_2$, which may be the same or different, are each selected from the group consisting of hydrogen and a hydroxy-protecting group.

19. The method of claim 18 wherein the compound is 2-methylene-19-nor-20(S)-25-methyl-1α-hydroxycalciferol.

20. The method of claim 18 wherein said effective amount comprises about 0.01 μg/day to about 100 μg/day of said compound.

21. A method of treating a cancerous disease comprising administering to a patient with said disease an effective amount of a compound having the formula:

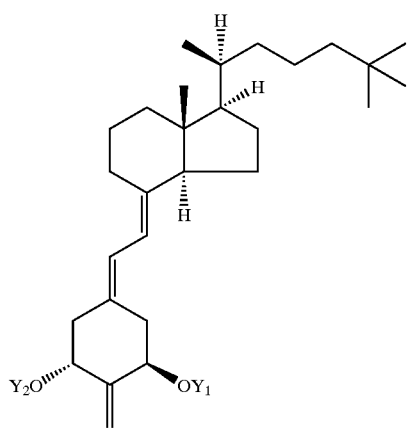

where $Y_1$ and $Y_2$, which may be the same or different, are each selected from the group consisting of hydrogen and a hydroxy-protecting group.

22. The method of claim 21 where the disease is leukemia.

23. The method of claim 21 where the disease is colon cancer.

24. The method of claim 21 where the disease is breast cancer.

25. The method of claim 21 where the disease is prostate cancer.

26. The method of claim 21 wherein the compound is administered orally.

27. The method of claim 21 wherein the compound is administered parenterally.

28. The method of claim 21 wherein the compound is administered transdermally.

29. The method of claim 21 wherein the compound is 2-methylene-19-nor-20(S)-25-methyl-1α-hydroxycalciferol.

30. The method of claim 21 wherein the compound is administered in a dosage of from 0.01 μg to 100 μg per day.

31. (20S)-de-A,B-25-methylcholestan-8-one having the formula:

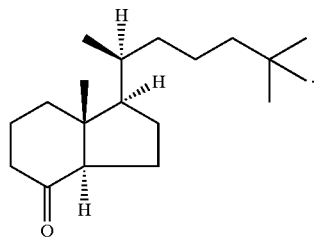

* * * * *